United States Patent [19]

Wismann

[11] Patent Number: 4,488,940
[45] Date of Patent: Dec. 18, 1984

[54] PROCESS FOR THE PRODUCTION OF DENTAL REPLACEMENT PARTS MADE OF METAL

[76] Inventor: Horst Wismann, Gartenstr. 22, D-8162, Schliersee, Fed. Rep. of Germany

[21] Appl. No.: 494,090

[22] Filed: May 12, 1983

[30] Foreign Application Priority Data

May 14, 1982 [DE] Fed. Rep. of Germany ....... 3218300

[51] Int. Cl.³ .......................... C25D 1/10; C25D 1/20
[52] U.S. Cl. ............................................. 204/4; 204/6
[58] Field of Search ..................................... 204/4, 9, 6

[56] References Cited

U.S. PATENT DOCUMENTS

| 1,082,058 | 12/1913 | Wanand | 204/4 |
| 2,569,453 | 10/1951 | Chester | 204/38 R |
| 2,682,500 | 6/1954 | Tanner | 204/6 |
| 2,834,052 | 5/1958 | Hunn | 204/6 |
| 2,841,548 | 7/1958 | Perlman | 204/4 |
| 3,431,183 | 3/1969 | Regan | 204/4 |
| 3,567,592 | 3/1971 | Wismann | 204/9 |
| 3,997,637 | 12/1976 | Rogers | 264/19 |

*Primary Examiner*—Thomas Tufariello
*Attorney, Agent, or Firm*—Cushman, Darby & Cushman

[57] ABSTRACT

For the production of dental replacement parts, a mold is produced from a starting model which mold is used for pouring a cast of the model with a low melting metal. After removal of the casting mold, this cast is inserted into a galvanic bath according to which the surfaces that are not to be coated, are covered up. At the exposed surfaces, a galvanic coating in the desired thickness is applied, whereupon the low melting metal is melted out. Dental replacement parts may be produced in this manner with a very high precision and considerable savings in material and operating time.

18 Claims, 7 Drawing Figures

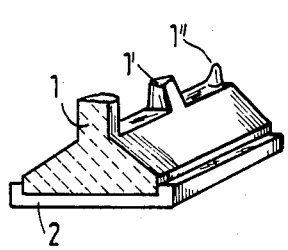
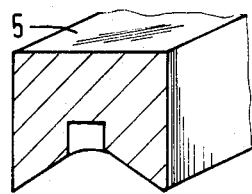
FIG.1A  FIG.1B  FIG.1C
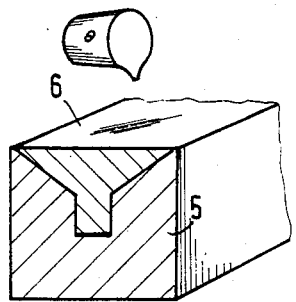
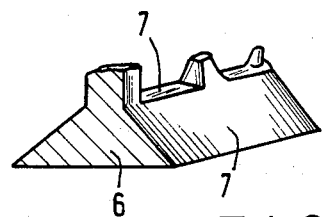
FIG. 2A  FIG. 2B
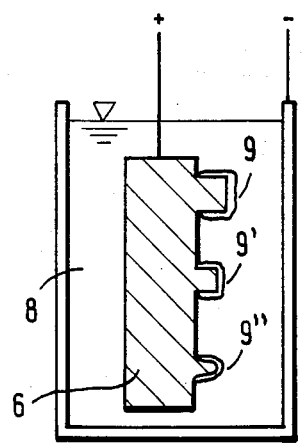
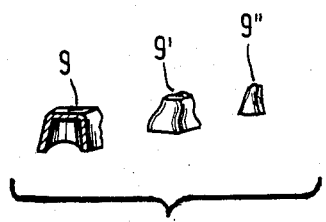
FIG. 3A  FIG. 3B

PROCESS FOR THE PRODUCTION OF DENTAL REPLACEMENT PARTS MADE OF METAL

PREAMBLE

The invention relates to a process for the production of dental replacement parts made of metal.

The process of making dental parts of metal mentioned has been used generally for many years in dental practice (cf. for example U.S. Pat. No. 2,980,998). At the same time, the cast produced as a rule from some noble metal and which is often made by a dental laboratory, is finished by hand in order to obtain a precisely fitting final replacement part for the tooth. One does not succeed in casting the high melting noble metal (for example, pure gold melts at 1064° C. and customary tooth gold alloys may have their melting points at about 960° C.) with such high precision that a reworking by hand can be omitted. Frequently, the cast is so imprecise that it is not usable and a new cast must be made. Often, the cast has casting faults, for example, shrink holes, and then too, it is necessary to produce a new cast. Beside these difficulties, it is disadvantageous that the cast, even if it is cast as a hollow body, requires a relatively high quantity of the expensive noble metal, because during casting one may not go below a certain thickness of the wall.

Because of the difficulties and disadvantages described, experts have been trying for a long time to create other processes for the production of dental replacement parts made of noble metal, which require less secondary work by hand an/or a lesser use of noble metal. Specifically processes have become known in the case of which the model is made electrically conductive on the surface and it is coated galvanically with a layer of noble metal and afterwards the base metal is removed from the body of noble metal produced in that way. At the same time, it is also possible to deposit ceramic material together with the noble metal (U.S. Pat. No. 3,567,592) or to apply it subsequently, whereby possibly the body of noble metal may be etched away (German OS No. 25 18 355). Although these processes avoid the difficulties and the high consumption of material of the noble metal casting basically, still they could not gain ground in practice because it is difficult to apply an electrically conductive layer so evenly and so thin on the model that it will cause no faults in molding, but nevertheless will ensure everywhere a sufficient and even galvanic deposit. Also as a result of the use of selected metallizing coating masses for dental purposes (U.S. Pat. No. 2,841,548), these difficulties could not be overcome. Especially, it is disturbing in the case of the known process described that for the production of the mass producing the surface electric conductivity, great care and manual dexterity are required because of the various anatomical shapes and nevertheless no satisfactory and sufficiently even results will be achieved.

The present invention starts out from the task of creating a simple and economic process for the production of dental replacement parts made of metal which process produces replacement parts with great evenness and reliability and of very great precision.

In the case of the process according to the invention, the difficulties of the casting of metal at a high temperature as well as the surface treatment of the predetermined anatomical forms for achieving electric conductivity are avoided. The process may be standardized and automated without trouble and requires for its execution merely average skills so that it may be carried out by trained personnel. The fitting metal part is obtained directly for, because of the high precision of the production process, any secondary finishing by hand is not necessary as a rule; in any case, occasionally quite slight reimprovement work may be effective or recommendable.

Since the cast is produced from a low melting, non-noble metal which is selected solely in view of its casting properties, even the cast will already have the desired high precision of form. To that comes the fact that the cast at low temperature produces lesser difficulties anyway and is more precise than the casting of high melting noble metals.

Because of the high precision of the metal parts produced according to the process of the invention, the galvanically produced metal layer may be kept considerably thinner than in the case of the traditional casting process, so that a very considerable saving of noble metal will result. In the case of the known noble metal casting, the minimum wall thickness of the cast blank of the dental replacement should be of 0.5 mm, because of the required strength and because for reworking by hand, sufficient material must be available. On the contrary, in the case of the process according to the invention, a wall thickness of about 0.1 to about 0.3 mm is sufficient because any reworking by hand with noticeable removal of material is not required, and because as a result of the structure of the metal part through galvanization, a higher strength of the metal will result. For example, according to the process of the invention, a tripartite bridge which, in the traditional noble metal casting technique requires about 10 g of gold, will be produced with only 2 to 4 g of gold; moreover, it has a very much better precision. Generally, it will be possible with the process according to the invention, to achieve a saving of gold of at least 50% as compared to the traditional noble metal casting technique.

It is self-understood that dental replacement parts produced according to the invention, just as well as traditional dental replacement parts, may be reinforced by metal put underneath, for example, plastic or porcelain against the loads occurring in use. Also the often customary additional coatings of plastic, porcelain and the like for the improvement of the appearance may be used in the case of dental replacement parts produced according to the invention.

A further important advantage of the process of the invention consists in the fact that because of the simple and easily standardizable operating steps, it can be carried out considerably more quickly than the traditional process for noble metal casting. Average dental laboratories reach a production of about 10 to 15 dental replacement members per man and day. With the process according to the invention on the contrary, one may easily achieve a production of about 160 members of dental replacements per man and day, therefore, more than ten times as many as with the traditional techniques. At the same time, the important advantage may be used that the galvanization which may, for example, require approximately ten hours, may be carried out overnight without supervision.

The saving of noble metal, the high production speed and the elimination of highly skilled, secondary finishing work leads altogether to a very considerable reduction of the production costs. In the case of the high prices, as is well known, for dental replacements, this is a very important advantage. Advantageous further developments of the process according to the invention are stated in the following description and claims.

BRIEF DESCRIPTION OF THE DRAWINGS

The process according to the invention will be explained in more detail for example, on the basis of the drawings.

FIG. 1A shows a model replacement part on a base; FIG. 1B shows the mold in place on the base; FIG. 1C shows the mold alone; and the casting mold produced by means of the model;

FIG. 2A shows the production of a cast from low melting metals by means of the casting mold and FIG. 2B shows the cast part; and FIGS. 3A and 3B show the production of a metal replacement part by means of galvanizing and melting away of the cast.

DETAILED DESCRIPTION

In FIG. 1, the numeral 1 is a model of the dental replacement part to be produced, whereby in the case of this embodiment, three replacement parts 1, 1' and 1" are to be produced simultaneously. The model may consist of gypsum or some other material and is produced in a known manner. In the case of the embodiment shown by way of example, crowns for strumps of teeth are to be produced. The model may however also have any other arbitrary form, depending on the metal part to be produced, for example, it may be a negative form instead of the positive form shown.

The model 1 will be attached effectively on a base 2. On the base 2, a container 3 enclosing the model will be disposed which is filled by way of a pouring-in opening 4 with suitable material, which solidifies. After solidification of this material and removal from the model 1, one will obtain a casting mold 5 which contains the reverse form of the model, in this case the negative form of the model 1.

An essential advantage will result, whenever the casting mold is produced of elastic plastic which is true to form. The use of an elastic plastic which is true to form offers the advantage that it will be possible easily to separate the casting mold 5 from the model 1 enclosed by it at first without there being any danger of damaging the casting mold thereby or to deform it lastingly. A two-component silicone rubber is used preferably for the casting mold 5. Such plastic may be produced easily and quickly by allowing a pourable starting mixture of the two components to harden. The hardening takes place quickly, for example, in 15 to 30 minutes.

Suitable plastics, especially the last mentioned two-component silicone rubber, are obtainable on the market, for example, from the firm S.W.S. Silicon Corporation, Adrian, Mich., U.S.A. In the case of casting of the casting mold 5, pressure or a vacuum is applied to the still liquid metal, so that an exact casting mold 5 free of bubbles will be obtained.

As a low melting metal, one may use a tin-lead-bismuth-cadmium-alloy with a melting range from 65° C. to 300° C., depending on the heat resistance of the material of the casting mold 5. A tin-lead-bismuth alloy melting at about 95° C. has turned out to be suitable. Preferably, the bismuth content amounts to about 1% by weight. Such alloys and other alloys with similar properties are known in the status of the prior art. As is well known, these alloys have the advantage that they make possible casts which are very true to form.

The cast 6 corresponding to the model 1 is covered up on the surfaces 7 which are not to be provided with a galvanic coating, for example, by a lacquer which may be painted onto the cast 6 and which is not taken off by the galvanic bath.

As FIG. 3 shows, the cast 6 pretreated in such a way, is then submerged into a galvanic bath 8, for example, into a gold sulfite bath. The predetermined metal, for example, gold is deposited from the bath onto the exposed metal surface of the cast 6 and thus forms the desired replacement part 9.

After conclusion of the galvanizing process, the casting material may easily be melted away by the action of heat, for example, in a melt bath by heating devices or the like. As a result of a chemical secondary treatment, possible remnants of the casting material may be removed from the metal part 9. It is however also possible to dissolve the cast 6 completely. In order that the surface of the galvanically produced layer of noble metal or of the metal part 9 does not change, for example change color, during removal of the cast 6, it will be effective to apply a protection layer onto the layer of noble metal which protective layer is constant during removal of the cast, but otherwise easily removable. The simplest method is to apply such a protective layer galvanically. Since the work is carried out galvanically anyway, it will be effective to apply a galvanic protective layer onto the metal part 9. The use of a protective layer made of nickel or of a nickel alloy is particularly simple. Such a protective layer may be applied easily galvanically and may again be removed easily by dissolution in an acid.

The replacement part 9 obtained in the case of the process of the invention is frequently provided for cosmetic reasons with a coating, for example, of porcelain, enamel, plastic or the like. In order to obtain a good connection of such a coating with the nobel metal 9, it will be possible to provide the latter with a surface promoting the adhesion of the coating. Techniques suitable for this purpose have been known, for example, from the German Pat. No. 728,497 and No. 880,783 and the U.S. Pat. No. 2,569,453. It is particularly simple to promote the adhesion of the coating through the fact that the noble metal layer is produced with a rough surface. This may be accomplished preferably through the fact that during the production of the noble metal layer, a first partial layer with a smooth surface and after that a second partial layer with a rough surface adhering firmly thereto is deposited electrolytically. The second partial layer may be deposited, for example, while increasing the density of the current or with the use of a bath without a grain refining agent. Preferably the first partial layer has a thickness of 0.05 to 0.2 mm and the second partial layer has a lesser thickness than the first partial layer. A relatively thin second partial layer will be sufficient in order to achieve the desired improvement of the adhesion, for example 5–50$\mu$.

The adhesion of a coating made of porcelain, ceramic, plastic and the like on the noble metal layer may be particularly well improved through the fact that before application of the coating, an intermediate layer of some other material is applied improving the adhesion of the coating. Suitable therefore all nickel and nickel alloys, especially the same materials which may also act in the case of removal of the casting as a protective layer. Suitable intermediate layer materials are also cited in the German OS No. 25 18 355. It will be advantageous to apply the intermediate layer galvanically, because the process contains some galvanic operating steps anyway. Often a further improvement of the adhesion of the coating will result, whenever one uses an intermediate layer oxidized after its application.

For the connection of a layer of gold, for example, with plastic, it will be possible to galvanize first of all a layer of gold onto the cast of low melting metal, whereupon a partial layer consisting of particles is galvanized on which consists a mixture of plastic and metal oxide or of the pertinent metal, which makes possible the galvanic deposit. These particles into the surface of the metallic dental replacement part produced in this way result in a good connection with the plastic applied then thereon, which plastic is of the same type as the one of the mixture cited previously. The portion of plastic in the mixture may amount up to 50%.

According to a second embodiment given by way of example, a coarser layer of gold is galvanized onto the layer of pure gold by means of another galvanic bath, which layer has a granular, microporous structure and in this way, a good connection with the plastic that is to be applied thereon will result.

The term "precious metal" used here is to be valid for all metallic materials which on the basis of their characteristics, especially of a good chemical constancy, are suitable for the use in dental replacement parts and which may be deposited galvanically. At the same time, we may be dealing with metals or with metal alloys with or without insertions of non-metallic substances (for example, according to the U.S. Pat. No. 3,567,592).

One advantage of the process according to the invention is that because of the easily removable, low melting metal, hollow spaces may also be formed easily. Thus, for example, a bridge may be developed partly in the shape of a hose, so that gold rests on the gum and no hollow space filled with plastic and open on the bottom exists. Furthermore, the process according to the invention permits the process of 99.9% gold, whereby a good strength of the replacement part produced in this way results as a consequence of the galvanic deposit. Finally, the process of the invention ensures a reproduction of the model with the highest precision.

In case that the low melting metal selected according to points of view of casting techniques should not be sufficiently homogenous, then first of all a thin nickel or copper layer may be galvanized onto the cast 6 which layer forms a homogenous conductor, whereupon then the layer of noble metal is galvanized on. This auxiliary layer of nickel or copper may subsequently be removed again from the finished dental replacement part after melting out of the cast 6.

The process described for the production of a metal replacement part 9 may not only be used in the dental field for bridges, crowns, fillings, prostheses and the like, but also for the production of jewelry and other molded parts to be produced on the basis of a model. At the same time, a layer with a thickness of up to 5 mm may be deposited galvanically depending on the purpose of use of the pertinent metal replacement part. For example, a steel plate may be produced by the process according to the invention which may be inserted as a prosthesis. By proper shaping of the model, it will be possible to also mold sliding joints or clamps galvanically onto this steel plate which serve for the connection with the dental replacement part.

Crowns or bridges produced by the process according to the invention are customarily filled with plastic.

The term "low melting metal" is to be understood in such a way that we are dealing with a low melting, electrically conductive material and we may also especially deal with a plastic permeated with metal particles. The materials used for the casting mold and the low melting cast are selected such that the casting mold keeps true to form in the case of the melting temperature of the casting material.

What I claim is:

1. In a process for the production of dental replacement parts of non-uniform shape made of precious metal, comprising the steps of producing a model of the replacement parts and, then, with the model, producing the casting mold from an elastic plastic and producing with the mold a cast of the dental replacement part at a casting temperature compatible with the plastic, and in producing the cast, using a metal having a melting point substantially lower than that of the precious metal, and then coating the cast galvanically with a layer of the precious metal and then removing the cast with the remaining layer being the dental replacement part.

2. The process as claimed in claim 1 wherein the thickness of the layer of precious metal is at least 0.05 mm.

3. The process as claimed in claim 1 wherein the thickness of the layer of precious metal is at most 5.0 mm.

4. Process as claimed in claim 1 wherein the elastic plastic is a two-component silicon rubber.

5. Process as claimed in claim 1 wherein the cast is produced with a metal alloy including tin, lead and bismuth having a melting point at approximately 95° C.

6. The process as claimed in claim 1 wherein the casting mold is produced under a vacuum.

7. The process as claimed in claim 1 including the step of removing the cast by melting it.

8. Process as claimed in claim 1 including the step of providing a protective layer to the layer of precious metal on the dental replacement part.

9. The process as claimed in claim 8 wherein the protective layer is applied galvanically to the layer of precious metal.

10. Process as claimed in claim 8 or 9 wherein protective layer is selected from the group consisting of nickel and nickel alloy.

11. Process as claimed in claim 1 wherein the replacement part is provided in partial areas with a coating including the step of applying to the layer of precious metal in the partial areas a surface promotiong the adhesion of the coating.

12. The process as claimed in claim 11 wherein during the production of the layer of precious metal, a first partial layer with a smooth surface and a second partial layer adhering thereto with a rough surface is deposited on the first surface electrolytically.

13. The process as claimed in claim 12 wherein the first partial layer produced with a thickness of 0.1 to 0.2 mm and the second partial layer is produced with a lesser thickness than the first partial layer.

14. The process as claimed in claim 1 wherein the replacement part is to be provided with a coating, an intermediate layer of a material improving the adhesion of the coating is applied.

15. The process as claimed in claim 14 wherein the intermediate layer is applied galvanically.

16. The process as claimed in claim 14 wherein the intermediate layer is oxidized after application.

17. The process as claimed in claim 1 wherein the precious metal is gold.

18. The process as claimed in claim 1 wherein the casting mold is produced under pressure.

* * * * *